US006486356B2

(12) United States Patent  
Bernard et al.

(10) Patent No.: US 6,486,356 B2
(45) Date of Patent: *Nov. 26, 2002

(54) PROCESS FOR THE PREPARATION OF 1-ARYL-3-CYCLOPROPYL-1,3-PROPANEDIONES

(75) Inventors: Didier Bernard, Lyons; Michel Casado, Saint Symphorien d'Ozon; Virginie Pevere, Lyons; Alain Truchon, Sathonay Camp, all of (FR)

(73) Assignee: Rhone-Poulenc Agro, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,175
(22) PCT Filed: Jul. 3, 1998
(86) PCT No.: PCT/EP98/04947
§ 371 (c)(1),
(2), (4) Date: Mar. 28, 2000
(87) PCT Pub. No.: WO99/02476
PCT Pub. Date: Jan. 21, 1999

(65) Prior Publication Data
US 2002/0002309 A1 Jan. 3, 2002

(30) Foreign Application Priority Data
Jul. 7, 1997 (GB) .............................................. 9714305

(51) Int. Cl.$^7$ .............................................. C07C 45/00
(52) U.S. Cl. ......................... 568/314; 568/309; 568/42
(58) Field of Search .............................. 568/42, 49, 43, 568/50, 306, 309, 313, 314, 315, 316

(56) References Cited

U.S. PATENT DOCUMENTS

| 3,742,062 A | * | 6/1973 | Chappelow, Jr. et al. |
| 3,929,451 A | * | 12/1975 | Cross et al. |
| 3,957,805 A | * | 5/1976 | Fanshawe et al. |
| 5,684,206 A | | 11/1997 | Casado et al. |
| 6,143,935 A | | 11/2000 | Boaz et al. |

FOREIGN PATENT DOCUMENTS

| EP | 0418175 | 3/1991 |
| EP | 0507013 | 10/1992 |
| EP | 0527036 | 2/1993 |
| EP | 0527037 | 2/1993 |
| EP | 0560482 | 9/1993 |
| EP | 0609798 | 8/1994 |
| EP | 0682659 | 4/1997 |
| GB | 1435639 | 5/1976 |
| WO | 98/55438 | 12/1998 |

OTHER PUBLICATIONS

Advanced Organic Chemistry (textbook) by J March, p. 368; Mc Graw–Hill Book Company, New York, 1968.*

CA:127:205564 abs of WO9727187, Jul. 1997.*

CA:123:143438 abs of EP625508, Nov. 1994.*

CA:120:164152 abs of JP 05202009, Aug. 1993.*

CA:108:55480 abs of J Org Chem by Gilbert et al. 53(2) pp 449–50 1988.*

CA:68:59059 abs of J Appl Chem by Haken et al 18(1) pp 17–19 1967.*

Cannon et al, *Journal of Organic Chemistry*, vol. 17, No. 5, May 1952, pp. 685–692, XP000573850.

* cited by examiner

Primary Examiner—Jean F. Vollano
(74) Attorney, Agent, or Firm—Burns, Doane, Swecker & Mathis, L.L.P.

(57) ABSTRACT

A process for preparing a compound of the formula:

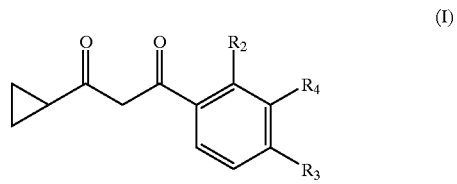

(I)

which comprises reacting a compound of the formula:

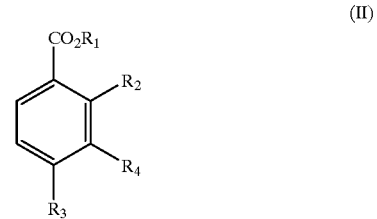

(II)

wherein $R_1$ is $C_{1-6}$ straight- or branched-chain alkyl, with a compound of the formula:

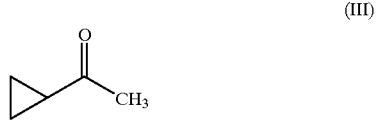

(III)

in an aprotic solvent in the presence of base.

12 Claims, No Drawings

PROCESS FOR THE PREPARATION OF 1-ARYL-3-CYCLOPROPYL-1,3-PROPANEDIONES

The present application is a 371 national stage application of International Application No. PCT/EP98/04947, published in English, Jan. 21, 1999 as WO 99/02476, which application claims priority based on Great Britain Application No. 9714305.1, filed Jul. 7, 1997.

This invention relates to a process for preparing 1,3-diketone compounds and the products obtained by this process. More particularly the invention relates to the preparation of intermediate compounds in the manufacture of pesticides.

Pesticidal 4-benzoylisoxazoles, particularly 5-cyclopropylisoxazole herbicides and intermediate compounds in their synthesis, are described in the literature, for example in European Patent Publication Nos. 0418175, 0527036, 0560482, 0609798 and 0682659. Various methods for preparing these compounds are known. The present invention seeks to provide an improved method for the preparation of intermediate compounds in their synthesis.

The present invention provides a process for the preparation of a compound of formula (I):

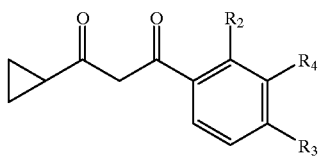

(I)

wherein:

$R_2$ is $C_{1-6}$ straight- or branched- chain alkylthio, $C_{1-6}$ alkyl, $C_{1-6}$ haloalkyl, $CH_2SR_5$, $C_{1-6}$ alkoxy, $C_{1-6}$ haloalkoxy, or halogen; or a N-linked imidazole, pyrazole, 1,2,3,4-tetrazole, 1,2,3-triazole or 1,2,4-triazole ring which ring systems are optionally substituted by one or more groups selected from halogen. $C_{1-6}$ alkyl, $C_{1-6}$ haloalkyl or $C_{1-6}$ straight- or branched- chain alkylthio;

$R_3$ is $C_{1-6}$ straight- or branched- chain haloalkyl, $C_{1-6}$ straight- or branched- chain alkyl, $C_{1-6}$ alkoxy, $C_{1-6}$ haloalkoxy, halogen, $C_{1-6}$ straight- or branched- chain alkylthio or nitro; or a N-linked imidazole, pyrazole, 1,2,3,4-tetrazole, 1,2,3-triazole or 1,2,4-triazole ring which ring systems are optionally substituted by one or more groups selected from halogen, $C_{1-6}$ alkyl, $C_{1-6}$ haloalkyl or $C_{1-6}$ straight- or branched- chain alkylthio.

$R_4$ is hydrogen, $C_{1-6}$ straight- or branched- chain haloalkyl, $C_{1-6}$ straight- or branched- chain alkyl, $C_{1-6}$ alkoxy, $C_{1-6}$ haloalkoxy, halogen. $C_{1-6}$ straight- or branched-chain alkylthio-, or a 5 or 6- membered heterocyclic ring (which may be unsaturated or partially saturated) containing 1 to 3 hetero atoms selected from oxygen, nitrogen and sulphur, optionally substituted by halogen. $C_{1-6}$ haloalkyl, $C_{1-6}$ alkyl, $C_{1-6}$ haloalkoxy, $C_{1-6}$ alkoxy $SO_nR_5$, nitro or cyano;

or $R_3$ and $R_4$ together with the carbon atoms to which they are attached, form a 5 to 7 membered saturated or unsaturated heterocyclic ring containing up to three ring heteroatoms selected from nitrogen, oxygen and sulfur, which ring is optionally substituted by one or more groups selected from halogen, nitro, $C_{1-6}$ straight- or branched-chain alkylthio, $C_{1-4}$ alkyl, $C_{1-4}$ alkoxy, $C_{1-4}$ haloalkyl, $C_{1-4}$ haloalkoxy, $=O$ and $=NO-R^5$.

$R_5$ represents $C_{1-6}$ straight- or branched- chain alkyl and n represents zero, one or two;

which process comprises the reaction of a compound of formula (II):

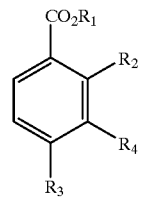

(II)

wherein $R_1$ is $C_{1-6}$ straight- or branched- chain alkyl, and $R_2$, $R_3$ and $R_4$ are as hereinbefore defined, with a compound of formula (III):

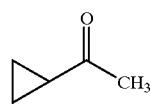

(III)

in an aprotic solvent in the presence of a base.

When $R_4$ represents a heterocyclic ring, preferred rings include 3-isoxazolyl, 5-isoxazolyl, 2-thiazolyl, 5-oxazolyl, 2-furyl, 3-furyl, 2-thienyl and 3-thienyl.

$R_1$ preferably represents methyl.
$R_2$ preferably represents methylthio or methylthiomethyl.
$R_3$ preferably represents trifluoromethyl or bromo.
$R_4$ preferably represents hydrogen.

In an especially preferred embodiment of the invention $R_1$ represents $C_{1-6}$ alkyl (methyl is most preferred);
$R_2$ represents methylthiomethyl;
$R_3$ represents bromo; and $R_4$ represents hydrogen.

In a most especially preferred embodiment of the invention $R_1$ represents $C_{1-6}$ alkyl (methyl is most preferred);
$R_2$ represents $C_{1-6}$ alkylthio (methylthio is most preferred);
$R_3$ represents $C_{1-6}$ haloalkyl (trifluoromethyl is most preferred); and $R_4$ represents hydrogen.

Using these reaction conditions it has been found that the reaction gives high yields of the desired final product.

Certain compounds of formula (I) and a number of processes for their preparation have been described in the European Patent Applications cited above. Compounds (II) are known or may be prepared by known methods. Compound (III) and methods for its preparation are known.

The aprotic solvents which may be used may be nonpolar or polar. Nonpolar aprotic solvents which are suitable include aromatic or aliphatic hydrocarbons, particularly toluene and xylenes (toluene is preferred); aromatic halogenated hydrocarbons (chlorobenzene is preferred) or ethers such as tert-butyl methyl ether, dioxan or tetrahydrofuran. Examples of suitable polar aprotic solvents include dimethylsulfoxide, N-methylpyrrolidinone, N,N-dimethylformamide or N,N-dimethylacetamide (dimethylsulfoxide and N-methylpyrrolidinone are preferred). Chlorobenzene and toluene are especially preferred because of the good results obtained, and cost and suitability of such solvents for large scale preparations.

Generally the reaction temperature used in the above process is from about 0° C. to the boiling point of the solvent, preferably from about 0° C. to about 100° C.; for non-polar solvents such as toluene or chlorobenzene a temperature of from about 40° C. to about 90° C. is especially preferred; whilst for polar aprotic solvents such as dimethylsulfoxide and N-methylpyrrolidinone a temperature of from about 20° C. to about 40° C. is especially preferred.

Generally the reaction takes place in the presence of a strong base which is most preferably selected from an alkoxide of an alkali or alkaline earth metal, notably sodium ethoxide, sodium methoxide, sodium or potassium t-butoxide; and a metal hydride (notably sodium hydride). Sodium methoxide is an especially preferred base for reasons of effectiveness in the reaction.

According to a preferred variant of the process of the present invention the reaction is performed with continuous distillation of the alcohol $R_1$—OH formed in the course of the reaction, at atmospheric pressure or under reduced pressure (preferably from 150 to 250 mbars). Alternatively the alcohol $R_1$—OH formed may be removed by the use of a suitable molecular sieve, for example a 4 Angstrom molecular sieve.

Compounds of formula (II) wherein $R_2$ represents $C_{1-6}$ alkylthio; $R_3$ represents $C_{1-6}$ haloalkyl and $R_4$ represents hydrogen may be prepared by the reaction of a compound of formula (IV):

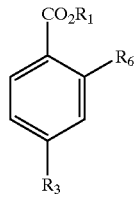

(IV)

wherein $R_1$ and $R_3$ are as defined above and $R_6$ represents a halogen atom selected from fluorine chlorine and bromine (preferably fluorine or chlorine), with an alkylthiol (or metal salt thereof) of formula $R_2$—X wherein $R_2$ is as defined above (preferably methylthio) and X represents hydrogen or an alkali metal (preferably sodium, potassium or lithium).

Preferably the above reaction to prepare intermediates of formula (II) is performed under substantially anhydrous conditions using a polar aprotic solvent preferably N-methylpyrrolidinone, acetonitrile or dimethylsulphoxide, at a temperature of from about −20° to about 150° C., preferably 0° to about 50° C.

The following non-limiting examples illustrate the invention.

EXAMPLE 1

Preparation of 1-cyclopropyl-3-(2-methylthio-4-trifluoromethylphenyl)propane-1,3-dione (small scale)

Sodium methoxide (3.51 g. 0.065M) was added to a mixture of methyl 2-methylthio-4-trifluoromethylbenzoate (12.5 g 0.050M) and cyclopropyl methyl ketone (7 ml, 0.070M) in toluene. The mixture was heated at 55–57° C. for 1 hour. Methanol was distilled under reduced pressure. After cooling to 20° C. the mixture was acidified and the organic phase washed (sodium bicarbonate solution and with water) and evaporated to give 1-cyclopropyl-3-(2-methylthio-4-trifluoromethylphenyl)propane-1,3-dione as yellow crystals (14.03 g), m.p. 64° C. A yield of 92.9% was obtained. The purity of the product was 95%.

EXAMPLE 2

Preparation of 1-cyclopropyl-3-(2-methylthio-4-trifluoromethylphenyl)propane-1,3-dione (large scale)

Sodium methoxide (64 g, 1.15M) was added to a mixture of methyl 2-methylthio-4-trifluoromethylbenzoate (200 g, 0.8M) in chlorobenzene (380 g). The mixture was heated to 75° C. and cyclopropyl methyl ketone (75 g, 0.88M) added during 2 hours whilst maintaining stirring at 75° C. After 4 hours methanol was distilled under reduced pressure. the mixture cooled to 50° C., and water followed by sulphuric acid (53 g of 36N) added. The organic phase was distilled under reduced pressure to give 1-cyclopropyl-3-(2-methylthio-4-trifluoromethylphenyl)propane-1,3-dione as yellow crystals (240 g), m.p. 58–60° C. A yield of 88% was obtained. The purity of the product was 90%.

EXAMPLE 3

Preparation of 1-cyclopropyl-3-(2-methylthio-4-trifluoromethylphenyl)propane-1,3-dione (small scale)

Sodium methoxide (0.54 g, 0.01M) was added to a mixture of methyl 2-methylthio-4-trifluoromethylbenzoate (1.25 g. 0.005M) and cyclopropyl methyl ketone (0.5 g, 0,006M) in anhydrous N-methylpyrrolidinone and heated at 30° C. for 3 hours. The cooled mixture was acidified, extracted (ether), washed (Water) and evaporated to give 1-cyclopropyl-3-(2-methylthio-4-trifluoromethylphenyl) propane-1,3-dione (1.43 g), m.p.68° C. in a yield of 94%. The purity of the product was greater than 95%.

The above experiment was repeated but replacing the N-methylpyrrolidinone by dimethylsulphoxide to give the desired product in a yield of 97%. The purity of the product was greater than 95%.

EXAMPLE 4

By proceeding according to the method described in Example 1 but using sodium methoxide (1.5 equivalents) and cyclopropyl methyl ketone (1.5 equivalents) and replacing the toluene by tert-butyl methyl ether, there was obtained. after 3 hours at 55° C. (with distillation of methanol), a 92% yield of 1-cyclopropyl-3-(2-methylthio-4-trifluoromethylphenyl)propane-1,3-dione (purity 95%).

EXAMPLE 5

By proceeding according to the method described in Example 1but using cyclopropyl methyl ketone (1.5 equivalents) and replacing the toluene by tetrahydrofuran, there was obtained, after 5 hours at 40° C. (without distillation of methanol), a 75% yield of the desired product.

REFERENCE EXAMPLE 1

Dry sodium thiomethoxide (0.385 g, 0.0055M) was added to a solution of methyl 2-chloro-4-trifluoromethylbenzoate (1.19 g, 0.005M) in anhydrous N-methylpyrrolidinone (10 ml) at 5° C. After 3 hours the mixture was acidified, extracted (ether), washed (water) and evaporated to give methyl 2-methylthio-4-trifluoromethylbenzoate (1.18 g, 94% yield), $^1$H NMR 2.44(s,3H), 3.89(s,3H), 7.33(1H), 7.41(1H), 8.02(1H).

What is claimed is:

1. A process for the preparation of a compound of formula (I):

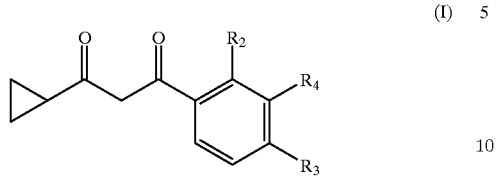

wherein:

$R_2$ is $C_{1-6}$ straight- or branched- chain alkylthio, $C_{1-6}$ alkyl, $C_{1-6}$ haloalkyl, $CH_2SR_5$, $C_{1-6}$ alkoxy, $C_{1-6}$ haloalkoxy, or halogen; or an imidazole, pyrazole, 1,2,3,4-tetrazole, 1,2,3-triazole or 1,2,4-triazole ring wherein a ring nitrogen is directly bonded to the benzene nucleus, which ring systems are optionally substituted by one or more groups selected from halogen, $C_{1-6}$ alkyl, $C_{1-6}$ haloalkyl or $C_{1-6}$ straight- or branched- chain alkylthio;

$R_3$ is $C_{1-6}$ straight- or branched- chain haloalkyl, $C_{1-6}$ straight- or branched- chain alkyl, $C_{1-6}$ alkoxy, $C_{1-6}$ haloalkoxy, halogen, $C_{1-6}$ straight- or branched- chain alkylthio or nitro; or an imidazole, pyrazole, 1,2,3,4-tetrazole, 1,2,3-triazole or 1,2,4-triazole ring wherein a ring nitrogen is directly bonded to the benzene nucleus, which ring systems are optionally substituted by one or more groups selected from halogen, $C_{1-6}$ alkyl, $C_{1-6}$ haloalkyl and $C_{1-6}$ straight- or branched- chain alkylthio;

$R_4$ is hydrogen, $C_{1-6}$ straight- or branched- chain haloalkyl, $C_{1-6}$ straight- or branched- chain alkyl, $C_{1-6}$ alkoxy, $C_{1-6}$ haloalkoxy, halogen, $C_{1-6}$ straight- or branched- chain alkylthio; or a 5 or 6-membered heterocyclic ring which may be unsaturated or partially saturated having 1 to 3 hetero atoms selected from oxygen, nitrogen and sulphur, optionally substituted by halogen, $C_{1-6}$ haloalkyl, $C_{1-6}$ alkyl, $C_{1-6}$ haloalkoxy, $C_{1-6}$ alkoxy, $SO_nR_5$, nitro or cyano; or $R_3$ and $R_4$ together with the carbon atoms to which they are attached, form a 5 to 7 membered saturated or unsaturated heterocyclic ring having up to three ring heteroatoms selected from nitrogen, oxygen and sulfur, which ring is optionally substituted by one or more groups selected from halogen, nitro, $C_{1-6}$ straight- or branched- chain alkylthio, $C_{1-4}$ alkyl, $C_{1-4}$ alkoxy, $C_{1-4}$ haloalkyl, $C_{1-4}$ haloalkoxy, $=O$ and $=NO-R^5$; and $R_5$ represents $C_{1-6}$ straight- or branched- chain alkyl; and n represents zero, one or two;

which process comprises reaction a compound of formula (II):

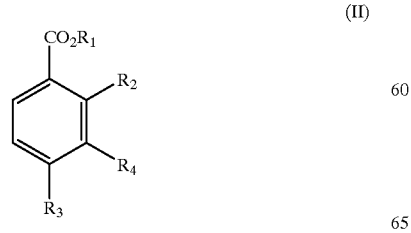

wherein $R_1$ is $C_{1-6}$ straight- or branched- chain alkyl, and $R_2$, $R_3$ and $R_4$ are as hereinbefore defined, with a compound of formula (III):

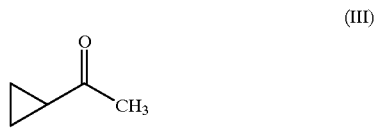

in an aprotic solvent in the presence of a base, wherein an alcohol $R_1OH$ formed during the reaction is removed by distillation or by a molecular sieve.

2. A process according to claim 1 wherein the solvent is toluene, chlorobenzene, dimethylsulfoxide or N-methylpyrrolidinone.

3. A process according to claim 1 wherein the base is selected from alkali metal and alkaline earth metal alkoxides and metal hydrides.

4. A process according to claim 1 in which $R_1$ represents $C_{1-6}$alkyl; $R_2$ represents methylthiomethyl; $R_3$ represents bromine and $R_4$ represents hydrogen.

5. A process for the preparation of a compound of formula (I):

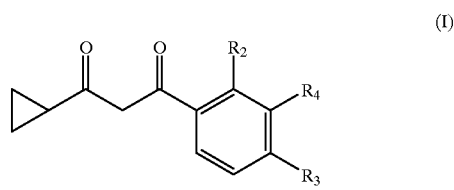

wherein:

$R_2$ is $C_{1-6}$ straight- to branched- chain alkylthio;

$R_3$ is $C_{1-6}$ straight- to branched- chain haloalkyl;

$R_4$ is hydrogen;

which process comprises reacting a compound of formula (II):

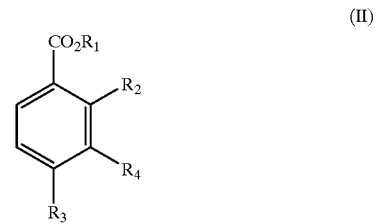

wherein $R_1$ is $C_{1-6}$ straight- or branched- chain alkyl, and $R_2$, $R_3$ and $R_4$ are as hereinbefore defined, with a compound of formula (III):

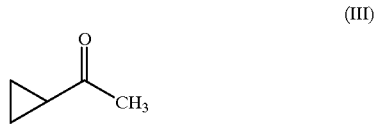

in a polar or nonpolar aprotic solvent in the presence of a base, wherein an alcohol $R_1OH$ formed during the reaction is removed by distillation or by a molecular sieve.

6. A process according to claim 5 wherein the solvent is toluene, chlorobenzene, dimethylsulfoxide or N-methylpyrrolidinone.

7. A process according to claim 5 wherein the base is selected from alkali metal and alkaline earth metal alkoxides and metal hydrides.

8. A process according to claim 5 wherein $R_1$ is methyl, $R_2$ is methylthio, $R_3$ is trifluoromethyl and $R_4$ is H.

9. A process according to claim 1 wherein the distillation is conducted on a continuous basis.

10. A process according to claim 1 wherein the alcohol is removed with a 4 angstrom molecular sieve.

11. A process according to claim 5 wherein the distillation is conducted on a continuous basis.

12. A process according to claim 5 wherein the alcohol is removed with a 4 angstrom molecular sieve.

* * * * *